(12) United States Patent
Bathurst et al.

(10) Patent No.: US 7,615,657 B2
(45) Date of Patent: Nov. 10, 2009

(54) METHOD OF PRODUCING AN OIL EXTRACT FROM SEEDS OF PLANTS VIA A BINARY AZEOTROPIC SOLVENT MIXTURE

(75) Inventors: Christopher Francis Bathurst, Christchurch (NZ); Graham Kennett, Christchurch (NZ); Lawrence Stephenson, Christchurch (NZ); Geoffrey Colin Tutty, Christchurch (NZ)

(73) Assignee: New Zealand Botanical Oils Ltd, Chistchurch (NZ)

( * ) Notice: Subject to any disclaimer, the term of this patent is extended or adjusted under 35 U.S.C. 154(b) by 607 days.

(21) Appl. No.: 10/502,566

(22) PCT Filed: Jan. 28, 2003

(86) PCT No.: PCT/NZ03/00006

§ 371 (c)(1),
(2), (4) Date: Oct. 26, 2004

(87) PCT Pub. No.: WO03/063885

PCT Pub. Date: Aug. 7, 2003

(65) Prior Publication Data

US 2005/0042347 A1    Feb. 24, 2005

(30) Foreign Application Priority Data

Jan. 28, 2002  (NZ) ..................... 516876

(51) Int. Cl.
*C11B 1/00*  (2006.01)
(52) U.S. Cl. ....................................... 554/12
(58) Field of Classification Search ............... 554/12
See application file for complete search history.

(56) References Cited

U.S. PATENT DOCUMENTS

| 4,298,540 A |   | 11/1981 | Youn et al. |
| 5,182,406 A | * | 1/1993 | Coenen ............... 554/13 |
| 5,281,732 A | * | 1/1994 | Franke ............... 554/16 |

(Continued)

FOREIGN PATENT DOCUMENTS

WO    WO-98/05294    *   2/1998

(Continued)

OTHER PUBLICATIONS

Fahey et al., Proc. Natl;. Acad. Sci., vol. 94, No. 19, pp. 10367-10372, 1997.*

(Continued)

*Primary Examiner*—Deborah D Carr
(74) *Attorney, Agent, or Firm*—Sughrue Mion, PLLC (57) ABSTRACT

The invention describes a method of producing extracts from the seeds of meadowfoam, brassicas and crambe plants. A number of subsidiary processes and steps are shown in order to extract differing fractions of oil. Products produced from the above method are also described including uses and methods of these products which include a variety of skin conditions including eczema, facial eczema, dermatitis, external ulcers, welts, rashes, insect bites, allergic reactions and other irritations, burns, wounds, psoriasis, acneiform eruptions, dryness, dry skin, irritation, skin atrophy, secondary infections and the like. The extracts are also described as being a useful compound for treatment of the symptoms of such skin conditions as described above. In particular the use and extraction of glucosinolate (GSL), thiocyanates (TCL) and isothiocyanates (ITCL) is described.

34 Claims, 5 Drawing Sheets

U.S. PATENT DOCUMENTS 5,955,623 A * 9/1999 Grant et al. .................. 554/224
6,136,330 A * 10/2000 Soliman et al. ............. 424/401
6,248,910 B1 * 6/2001 Franke ......................... 554/12

FOREIGN PATENT DOCUMENTS

| WO | WO98/05294 | * | 2/1998 |
| WO | WO00/25739 | * | 5/2000 |
| WO | WO 00/30602 A1 | | 6/2000 |
| WO | WO-00/30603 | * | 6/2000 |
| WO | WO-01/24617 | * | 4/2001 |
| WO | WO 01/24617 A1 | | 4/2001 |

OTHER PUBLICATIONS

Abstract of JP2001302490, 2001.*
Farley et al., Proc. Natl. Acad. Sci., vol. 94, No. 19, pp. 10367-10372, 1997.*
Mayo Clinic Staff, MayoClinic.com, "Dry skin", 2008.*
Derwent Abstract Accession No. 2001-475797/51, (B05), WO 200145661-A2, Jun. 28 2001.
Derwent Abstract Accession No. 2002-134662/18, JP 2001302490-A, Oct. 31, 2001.
Derwent Abstract Accession No. 2003-077920/08, EP 1262167-A1.

* cited by examiner

FIGURE 7

METHOD OF PRODUCING AN OIL EXTRACT FROM SEEDS OF PLANTS VIA A BINARY AZEOTROPIC SOLVENT MIXTURE

TECHNICAL FIELD

In one embodiment of the present invention, the invention relates to an extract from meadowfoam, brassicas or crambe seeds containing glucosinolates (GSL). More specifically the extract also contains GSL hydrolysis compounds including isothiocyanate (ITCL) and thiocyanate (TCL). The invention further relates to uses of the extract and skin condition treatments.

BACKGROUND ART

Meadowfoam oil from the seed of *Limnanthes alba* is known to have a number of uses. As it is a particularly stable oil it is often used as a base compound, or as an additive to oils and lotions. It has been used, for example, in soaps, massage oils, aromatherapy oils, and cosmetics. Generally, it is regarded as having 98% fatty acids and a superior stability over base oils and its use to date has been for these properties.

Similar materials such as brassicas and crambe seeds also have similar uses and properties.

Recent uses of the oil have extended to cooling oils, for food production and as a lubricant.

WO 01/24617 discloses use of a mutant form of meadowfoam plant, containing low erucic acid, which is particularly useful for cooking food production and as a lubricant.

U.S. Pat. No. 6,136,330 and WO 98/05294 disclose the use of this oil as an enhancing component for an aqueous liquid composition for skin treatment.

In WO 00/25739 meadowfoam oil or its derivatives were disclosed for use in increasing the deposition of vitamins and their precursors on the skin.

Not recognised by the prior art is the fact that meadowfoam oil (as well as the oil extracted from brassicas seeds and crambe seeds) contains glucosinolate compounds (GSL) and its hydrolysis derivative compounds, thiocyanate (TCL) and isothiocyanate (ITCL). The majority of patents relating to GSL, TCL and ITCL derive these compounds from *Cruciferae* species for use in anti-microbial preservative applications. In fact, most patents that discuss GSL, TCL and/or ITCL treat such compounds as a problem as ingestion appears to result in illness. This is of particular concern for crops used for stock feed.

Skin Conditions

Many oils, and/or essential oils, used either as oils, creams or lotions have been used to treat various skin complaints ranging from psoriasis, eczema, and generally rough skin. The action of the oil is to act as a moisturiser by acting as a barrier to prevent water loss from the skin. While moisturising the skin is important for most skin complaints, the oils seldom treat the underlying cause of the skin condition. They also do not necessarily stop the symptoms of such conditions such as itching.

The range of possible skin conditions which are treatable with varying degrees of efficacy by current topical applications or ingested drugs can include: eczema, facial eczema, dermatitis, external ulcers, welts, rashes, insect bites, allergic reactions and other irritations, burns, wounds, psoriasis, acneiform eruptions, dryness, dry skin, irritation, skin atrophy, secondary infections and the like.

Such conditions are treatable by a huge range of drugs from simple oils/fats/waxes through to steroids and cortisone derivatives, etc. Frequently such products will address the symptoms but not the underlying causes of the problem and thus the problem recurs.

Some of the powerful pharmaceutical drugs can have extreme side effects, which in themselves need further treatment.

However, some of the conditions are ones in which only the symptoms can be treated, but not the underlying cause.

Psoriasis in particular, is a very difficult condition to treat and various methods are currently in use including tar product creams, cortisone creams and UV treatment. These methods have numerous drawbacks such as; tar products are highly coloured, very messy, and have an unpleasant odour; cortisone creams are hard on the skin and have all the drawbacks of steroids; UV treatment is time consuming and must carefully be monitored to avoid skin cancers.

One patent that most closely describes topical agents using TCL only is U.S. Pat. No. 6,346,258. This patent describes topical agents containing thiocyanate ions and urea for enhancing the skins defense against chemical and physical irritations. The aim of the combination of thiocyanate ions and urea is to provide an improved effective agent for the prophylaxis of skin lesions for skin protections. The patent does not address psoriasis treatments in particular, there is a need for extra ingredients (urea); and further, the patent specifically excludes the use of organic TCL compounds, making the product a non-natural type remedy.

It is an object of the present invention to provide a processed oil and by-product that addresses all of the above problems.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

It is an object of the present invention to address the foregoing problems or at least to provide the public with a useful choice.

Further aspects and advantages of the present invention will become apparent from the ensuing description which is given by way of example only.

DISCLOSURE OF INVENTION

According to one aspect of the present invention there is provided a method of producing an oil extract from seeds of plants selected from the group including: meadowfoam; brassicas; crambe; said method including the steps of:
(a) washing the seed with a solvent, whereby oil from the seed is dissolved in the solvent; and
(b) separating the spent seed and the solvent solution; and
(c) distilling the solvent solution to obtain an oil extract from the solvent.

Preferably the distillation is completed at a temperature of equal to or less than 120° C. Preferably also the distillation is carried out under a vacuum, most preferably a vacuum with a pressure equal to or less than 50 kPa.

According to another aspect of the present invention there is provided the method of extraction as disclosed above, wherein said solvent is selected from the group: alcohol; hexane; heptane; aliphatic solvents; ethers; chlorinated solvents; chloroform; tricholoroethylene; carbon dioxide; and a combination thereof.

Preferably the solvent is hexane.

In an alternative embodiment, the solvent is preferably a binary azeotropic mixture of aliphatic solvents and alcohols. Preferably, it is a mixture of hexane and ethanol. Most preferably this mixture is approximately 79% hexane and 21% ethanol.

In preferred embodiments, the solvent distilled from the oil extract in step (c) is recycled into the solvent wash at step (a).

According to another aspect of the present invention there is provided the method of extraction as described above wherein before the step of washing the seed, step (a), the seed is dressed and dried.

According to another aspect of the present invention there is provided the method of extraction as described above wherein, before the step of washing the seed, step (a), a further step is included said step being: crushing the seed.

Preferably the seed is crushed to a flaked condition.

Optionally, subsequent to all the above steps, the oil extract is stored and allowed to settle so that seed husk residue can be filtered from the oil.

Preferably also any adverse odours remaining from the use of the solvent extraction process are removed by a further step of deodorising the oil extract. Optionally, said method of deodorising includes the step of adding water to the oil extract and subsequently boiling off the water and residual solvent, leaving a deodorised oil extract.

Optionally, or additionally, the oil is boiled off in an oven heated to a temperature less than 120° C. (preferably 80° C.). In addition, or as an alternative, a masking substance such as perfume can be added to mask the residual smells.

According to another aspect of the present invention there is provided the method of extraction of oil as described above wherein the solvent laden seed is dried to separate remaining solvent as condensate from spent seed husks. Optionally, the drying is by a combination of steam treatment, under a vacuum, and the application of heat, to produce dried spent seed husks.

In preferred embodiments, the condensate from the drying process is added to the oil extract during the settling process to collect any additional active fractions removed from the spent seed husks during drying.

According to a further aspect of the present invention there is provided a method of producing an oil extract substantially as described above wherein the oil extract contains glucosinolates (GSL). Preferably the oil extract also contains GSL hydrolysis compounds isothiocyanate (ITCL) and thiocyanate (TCL). Preferably also, the oil extract also contains nitrile thiones and phenolic compounds (flavanoids).

According to another aspect of the present invention there is provided an oil extract, produced in accordance with the method of extraction as described above.

According to another aspect of the present invention there is provided an oil extract containing glucosinolates (GSL), wherein the oil is extracted in accordance with the method of extraction as described above. Preferably the oil extract also contains GSL hydrolysis compounds isothiocyanate (ITCL) and thiocyanate (TCL). Preferably also, the oil extract also contains nitrile thiones and phenolic compounds (flavanoids).

According to a further aspect of the present invention there is provided a method of producing a light oil fraction from seeds of plants selected from the group including: meadowfoam; brassicas; crambe; the method including the steps of:
(d) mixing the oil extract as described above with a solvent selected from the group including: alcohol; water; and combinations thereof; and
(e) separating the solvent solution and oil; and
(f) drying the solvent solution from step (e) to remove the solvent and collecting the light oil fraction.

Preferably, the amount of solvent mixed with the extract oil is in an approximately equal volume.

Preferably the alcohol is selected from the group including: methanol; ethanol; other lower alcohols; and combinations thereof.

Preferably, where water is used as the solvent, water is the only solvent and no alcohol is used.

Optionally the above steps are repeated one or more times so that the oil from step (e) is mixed with further solvent in step (d) to obtain more light oil fraction in step (f).

According to a further aspect of the present invention there is provided a method of producing a light oil fraction from seeds of plants selected from the group including: meadowfoam; brassicas; crambe; the method including the steps of:
(g) mixing the oil extract a described above with at least one alcohol; and
(h) separating the alcohol solution of step (g) from the oil; and
(i) further mixing the oil from step (h) with at least one other alcohol to that used in step (g); and
(j) separating the alcohol solution of step (i) from the oil; and
(k) drying the alcohol solution from step (h) and the alcohol solution from step (i) either separately or together to remove the alcohol solvent and collecting the light oil fraction.

Preferably, the amount of alcohol mixed with the oil extract in steps (g) and (i) is in an approximately equal volume.

Most preferably the alcohol in step (g) is methanol and the alcohol in step (i) is ethanol.

According to a further aspect of the present invention there is provided a method of extraction of a light oil fraction substantially as described above wherein the light oil fraction contains glucosinolates (GSL). Preferably the light oil fraction also contains GSL hydrolysis compounds isothiocyanate (ITCL) and thiocyanate (TCL). Preferably also, the light oil fraction produced by the method above also contains nitrile thiones and phenolic compounds (flavanoids).

According to another aspect of the present invention there is provided a light oil fraction, wherein the fraction is extracted in accordance with the method of extraction as described above.

According to another aspect of the present invention there is provided a light oil fraction containing glucosinolates (GSL) wherein the light oil fraction is extracted in accordance with the method of extraction as described above. Preferably the light oil fraction also contains GSL hydrolysis compounds isothiocyanate (ITCL) and thiocyanate (TCL). Preferably also, the light oil fraction also contains nitrile thiones and phenolic compounds (flavanoids).

According to a further aspect of the present invention there is provided a method of producing a therapeutic aqueous solution from the seeds of plants selected from the group including: meadowfoam; brassicas; crambe; the method including the steps of: mixing the oil extract of step (c) with a base aqueous solution.

Optionally, the light oil fraction, substantially as described above is also mixed into the base aqueous solution.

Preferably the oil extract, and light oil fraction if present, forms 1 to 50% wt of the combined mixture.

Preferably, the base aqueous solution has a water component and this water component is the solvent solution from step (e) where water is used as the solvent.

Preferably, the base aqueous solution is a cream or ointment.

According to a further aspect of the present invention there is provided a method of producing a therapeutic aqueous solution substantially as described above wherein the therapeutic aqueous solution contains glucosinolates (GSL). Preferably the oil extract also contains GSL hydrolysis compounds isothiocyanate (ITCL) and thiocyanate (TCL). Preferably also, the therapeutic aqueous solution produced by the method above also contains nitrile thiones and phenolic compounds (flavanoids).

According to another aspect of the present invention there is provided a medicament, wherein the medicament is produced in accordance with the method as described above.

According to another aspect of the present invention there is provided a therapeutic aqueous solution containing glucosinolates (GSL) wherein the therapeutic aqueous solution is produced in accordance with the method as described above. Preferably the therapeutic aqueous solution also contains GSL hydrolysis compounds isothiocyanate (ITCL) and thiocyanate (TCL). Preferably also, the therapeutic aqueous solution also contains nitrile thiones and phenolic compounds (flavanoids).

According to a further aspect of the present invention there is provided a method of producing an oil solution from the seeds of plants selected from the group including: meadowfoam; brassicas; crambe; the method including the steps of: mixing the extract solution of step (e) where ethanol is used as the solvent, with a canola oil and then evaporating this mixture to remove the ethanol and leave an oil solution.

According to a further aspect of the present invention there is provided a method of producing an oil solution from the seeds of plants selected from the group including: meadowfoam; brassicas; crambe; the method including the steps of: mixing the extract solution of step (e) where ethanol is used as the solvent, with the oil extract from step (c) and then evaporating this mixture to remove the ethanol and leave an oil solution.

According to another aspect of the present invention there is provided an oil solution, wherein the oil solution is produced in accordance with the method as described above.

According to another aspect of the present invention there is provided an oil solution containing glucosinolates (GSL) wherein the oil solution is produced in accordance with the method as described above. Preferably the oil solution also contains GSL hydrolysis compounds isothiocyanate (ITCL) and thiocyanate (TCL). Preferably also, the oil solution also contains nitrile thiones and phenolic compounds (flavanoids).

The use of a compound including: an oil extract as described above; a light oil fraction as described above; a medicament as described above; an oil solution as described above; and combinations thereof; for treatment of a skin condition selected from the group including: eczema, facial eczema, dermatitis, external ulcers, welts, rashes, insect bites, allergic reactions and other irritations, burns, wounds, psoriasis, acneiform eruptions, dryness, dry skin, irritation, skin atrophy, secondary infections and the like; and combinations thereof.

The use of a compound including: an oil extract as described above; a light oil fraction as described above; a medicament as described above; an oil solution described above; and combinations thereof; for treatment of the symptoms of a skin condition selected from the group including: eczema, facial eczema, dermatitis, external ulcers, welts, rashes, insect bites, allergic reactions and other irritations, burns, wounds, psoriasis, acneiform eruptions, dryness, dry skin, irritation, skin atrophy, secondary infections and the like; and combinations thereof.

According to yet a further aspect of the present invention there is provided the use substantially as described above wherein the compound is combined with a pharmaceutically and physiologically acceptable carrier.

According to a yet further aspect of the present invention there is provided the use of a compound substantially as claimed above in combination with UV treatment.

A method of treatment of a skin condition selected from the group including: eczema, facial eczema, dermatitis, external ulcers, welts, rashes, insect bites, allergic reactions and other irritations, burns, wounds, psoriasis, acneiform eruptions, dryness, dry skin, irritations, skin atrophy, secondary infections and the like; and combinations thereof, by topical application of a compound including: an oil extract as described above; a light oil fraction as described above; a medicament as described above; an oil solution as described above; and combinations thereof.

A method of treatment of a the symptoms of a skin condition selected from the group including: eczema, facial eczema, dermatitis, external ulcers, welts, rashes, insect bites, allergic reactions and other irritations, burns, wounds, psoriasis, acneiform eruptions, dryness, dry skin, irritations, skin atrophy, secondary infections and the like; and combinations thereof, by topical application of a compound including: an oil extract as described above; a light oil fraction as described above; a medicament as described above; an oil solution as described above; and combinations thereof.

According to yet a further aspect of the present invention there is provided a method of treatment wherein the compound is combined with a pharmaceutically and physiologically acceptable carrier.

According to a yet further aspect of the present invention there is provided a method of treatment substantially as described above in combination with UV treatment.

According to a yet further aspect of the present invention, there is provided a medicament including a therapeutic amount of glucosinolate (GSL).

Preferably also, the medicament as described above also contains (GSL) hydrolysis compounds, isothiocyanate (ITCL) and thiocyanate (TCL).

Preferably also, the medicament as described above also contains nitrile thiones and phenolic compounds (flavonoids).

Preferably also, the medicament as described above is combined with a pharmaceutically and physiologically acceptable carrier.

According to a yet further aspect of the present invention there is provided the use of a medicament substantially as described above, for treatment of skin conditions selected from the group including: eczema, facial eczema, dermatitis, external ulcers, welts, rashes, insect bites, allergic reactions and other irritations, burns, wounds, psoriasis, acneiform eruptions, dryness, dry skin, irritations, skin atrophy, secondary infections and the like; and combinations thereof.

According to a yet further aspect of the present invention there is provided the use of medicament substantially as described above, for treatment of symptoms of a skin conditions selected from the group including: eczema, facial eczema, dermatitis, external ulcers, welts, rashes, insect bites, allergic reactions and other irritations, burns, wounds, psoriasis, acneiform eruptions, dryness, dry skin, irritations, skin atrophy, secondary infections and the like; and combinations thereof.

Preferably, the skin to which the composition is applied is the skin of an animal, most preferable a human. It will be appreciated by those skilled in the art that animals may be treated in the same manner as humans, for example facial eczema in stock animals.

According to a yet further aspect of the present invention there is provided a solid composition comprising dried, spent seed husks in the above described method.

From the above description the oil extraction method and product from meadowfoam, brassicas and/or crambe seeds, with its inherent properties of the compounds it contains and its stability, it can be seen that new and unexpected uses are produced by the intrinsic properties of the extracts. The solvent extracted oil can be used on its own or in a composition for the treatment of a wide range of skin conditions, the treatment occurring with no known side effects other than the improvement or disappearance of the skin condition.

BRIEF DESCRIPTION OF DRAWINGS

Further aspects of the present invention will become apparent from the ensuing description which is given by way of example only and with reference to the accompanying drawings in which.

BEST MODES FOR CARRYING OUT THE INVENTION

Extraction Example 1

Figure 1:
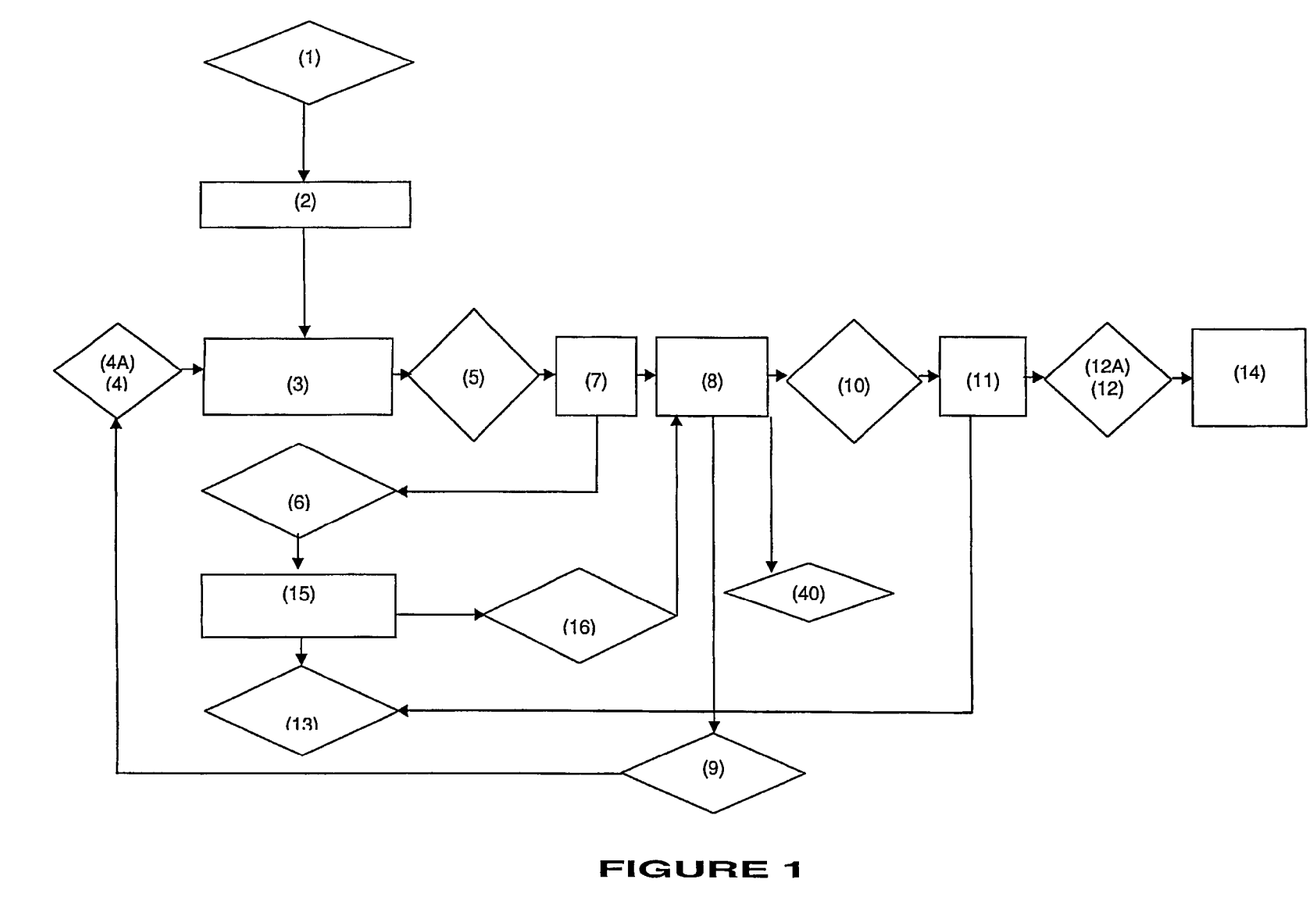
FIG. 1 is a process flow diagram for the production of an oil extract in one embodiment of the invention.

Referring to FIG. 1, preferably meadowfoam seed (1) is used in a dressed dry condition. This can be achieved by cleaning and air drying the seed (not shown), if this is not done at seed harvest.

A flat roll crusher is used to crush (2) the seed to a flaked condition. The flaked seed is then washed (3) one or more times in solvent (preferably hexane) (4). This dissolves the oils (5) from the seed (6) into the solvent (hexane) (4).

The step of crushing the seeds (2) can be omitted. However, in practice it has been found that omission produces a lower oil yield.

The seed (1) can also be cooked (not shown) before being extracted, or before being crushed (2). However, unless it is done to aid other aspects of the process (purification), the yield is not otherwise improved.

The solvent oil mixture is separated from the seed material (6) by filtration (7) (of known type).

Solvent distillation (8) is conducted to extract any remaining solvent (9) in the oil (5) at a temperature above the boiling point of the solvent (4) and below that of the oil (5). The purified solvent (9) can then be recycled for further use. In practice it has been found that for hexane, the temperature is best kept below 120° C. and the distillation (8) conducted under a partial vacuum of approximately 50 kPa.

In practice it has been found that the percentage yield of oil extract (12) is between 22 to 30%, most commonly 27% of dry yield (by weight). The oil extract (12) obtained is a dark greenish amber liquid.

Other solvents (4) can be used instead of hexane. However, in practice it has been found that this achieves the greatest yield of oil extract (12).

After solvent extraction (8), under distillation, the oil extract (10) is allowed to stand (11), to settle any fine seed husk residue (13) Further filtration (not shown) to remove any residue or other suspended solids can also be conducted (in known manner).

Any remaining adverse odours in the oil extract (12) can be removed in a number of ways (14): any residual hexane can be boiled off with water. The oil extract (12) can be oven heated to 120° C., which also has the advantage of removing any further water impurity. Perfume (not shown) of known type (for example, lavender oil) can be used to mask residual solvent smells.

The oil extract (12) is stored in suitable containers, which require no special storage conditions.

The solvent laden seed husks (15) are dried for recovery of further solvent and active ingredient as a condensate (16). They can be air-dried, but are preferably dried with a combination of steam treatment, vacuum and heat (to temperatures described above, less than 120° C., and a vacuum of 50 kPa). Condensate (16) is preferably collected from this process and added to the solvent distillation (18) step.

The dried spent husks (13) can be further pulverised (not shown) to provide a granulated powder if required.

1.1 Skin Treatment 1.1.1 Psoriasis

The oil extract (12), after extraction (8) and filtration (11) as described above was used to treat an existing skin condition of longstanding psoriasis. The skin condition produces red, raw, weeping skin, which no steroid would successfully treat. With application daily, of no more than required amount to cover the affected area, reduced the weeping skin to healing red skin which eventually left only a mild scar after approximately two weeks. In further experiments conducted by the applicant, this oil extract (12) has been found to be active against most mild to moderate forms of psoriasis.

1.1.2 Welts

A subject with white welts of unknown origin treated the welts daily by rubbing no more than a required amount of the oil extracted (12) as above onto the welts. After two weeks they were healing red scars.

1.1.3 Hand Cracks

Permanent deep cracks in the skin on the hands of one person topically applied the oil extracted (12) as above daily. In time the cracks had healed to red lines only.

1.1.4 Rough and Dry Skin

A large patch of rough and dry skin on a leg of one person, which has resisted treatment by other compounds treated the skin with the oil extracted (12) as described above intermittently. After a week the rough and dry skin was reduced in area by three-quarters.

1.1.5 Heel Cracks

Cracks in the heels of feet of one person, that resisted other types of treatment was treated using the oil extract (12) as above for a week. The cracks healed leaving a light colour on the skin.

Extraction Example 2

Figure 2:
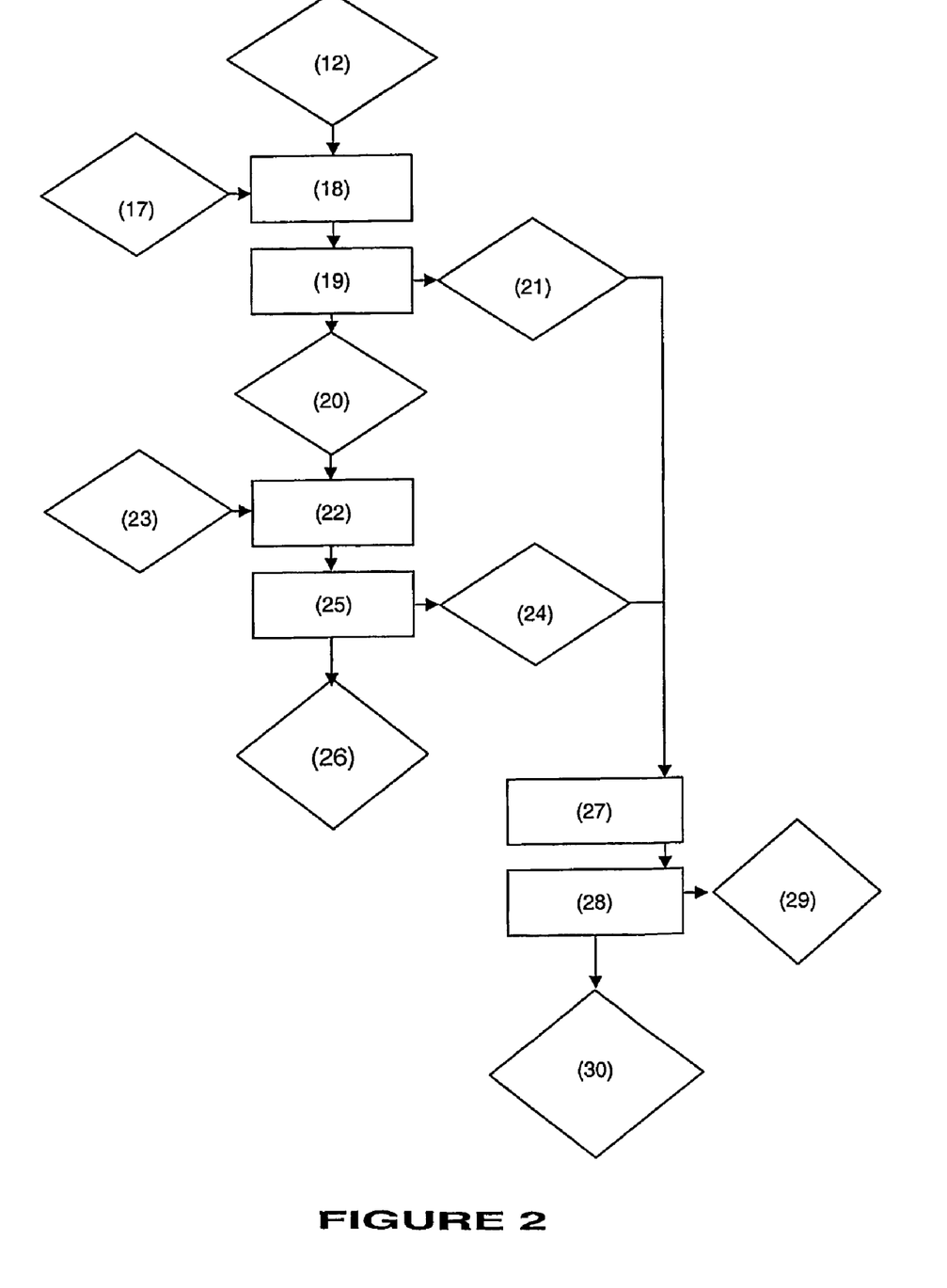
FIG. 2 is a process flow diagram for a further extraction step to produce a light oil fraction rich in GSL, ITCL and TCL compounds.

The oil extract from Example 1 is further processed as shown in FIG. 2. The oil extract (12) is mixed (18) with an approximately equivalent quantity of methanol (17). The mixture is then separated (19) (by known means) and both the oil (20) and methanol (21) portions are collected. The oil portion (20) is then mixed (22) again with an approximately equivalent portion of ethanol (23) in a similar manner and once again the ethanol (24) oil (26) mixture is separated (25).

The resulting methanol (21) and ethanol (24) solutions are then mixed (27) and dried (28).

Based on infra-red spectrophotometer analysis, light oil fractions (30) remain after drying (28) that are rich in GSL, TCL and ITCL compounds corresponding to infra-red absorption peaks at 2100 wavenumber indicating ITCL, 1260 and 1240 wavenumber indicating sulphonic bonds and 1040 wavenumber indicating sulfoxide bonds corresponding to GSL.

2.1 Skin Treatment

2.1.1 Psoriasis

The light oil fractions extracted from the methanol/ethanol mixture as well as the oil after alcohol extraction was used to treat an existing psoriasis condition. The results showed a healing effect for the light oil fraction separated using the alcohol extractions and the oil after extraction had no effect on the psoriasis.

Extraction Example 3

Referring to FIG. 1 and Example 1 above, the same process is used for producing an oil extract (12A) as in Example 1, however the solvent (4A) used is a binary azeotropic mixture of hexane (79%) and ethanol (21%).

3.1 Skin Treatment

3.1.1 Psoriasis

The oil extract (12A) from the process was used to treat an existing psoriasis condition. The results showed a significantly improved healing effect that was as much as three times more effective than the oil extract (12) of example 1 in treating the symptoms of psoriasis.

Extraction Example 4

Figure 3:
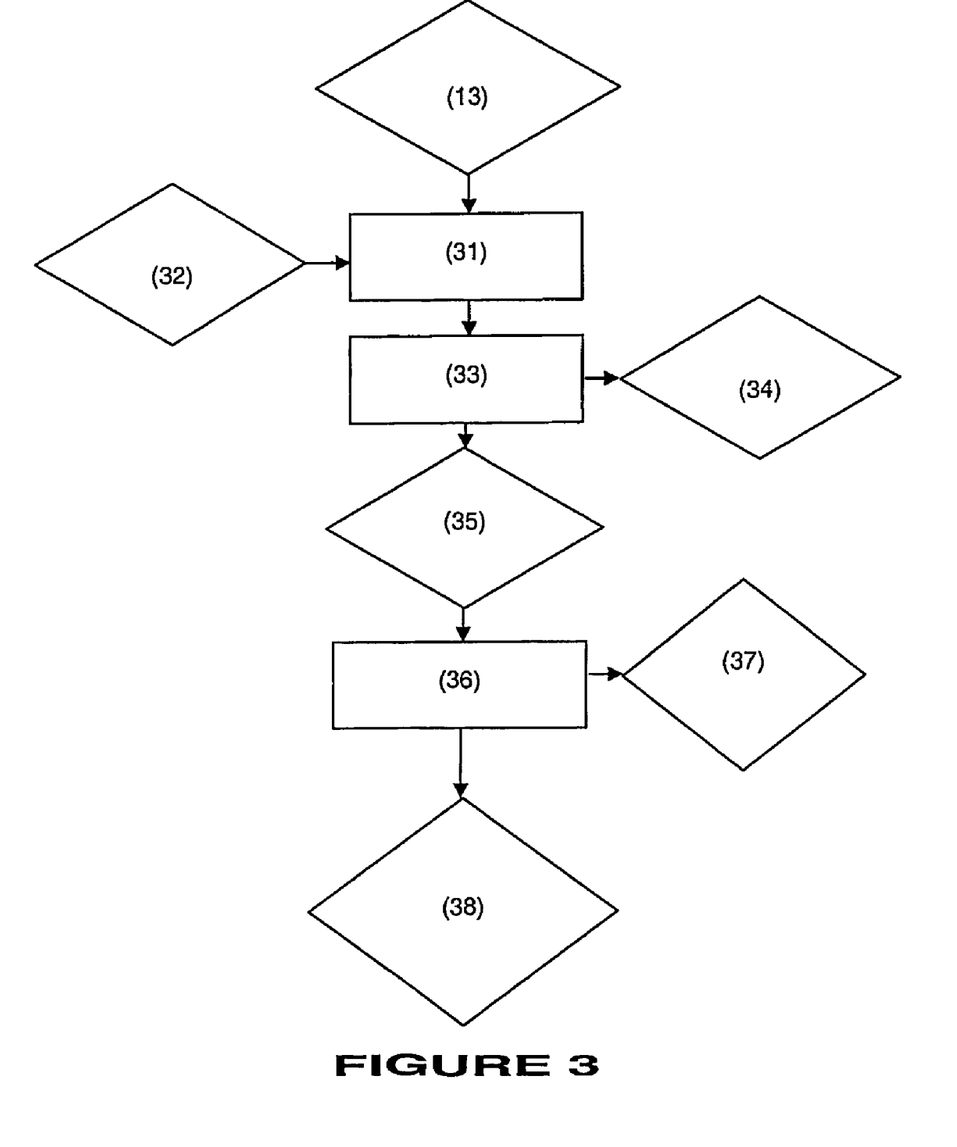
FIG. 3 is a process flow diagram for an alternative further extraction step to produce a light oil fraction rich in GSL, ITCL and TCL compounds.

Referring to FIG. 3, the dried seed husks (13) produced in Example 1 was further mixed (31) with ethanol (32) and allowed to settle. After settling the ethanol solution (35) was decanted off (33) from the seed (34) and dried (36).

The dried solution (38) was analysed using an infra-red absorption device and absorption was noted at 1490 and 1510 wave number indicating benzene ring overtones and 1020 and 1080 wavenumber indicating sulfoxide absorption. These peaks again suggest that GSL, ITCL and TCL compounds were present in the extracted seeds (13) hence the additional step in FIG. 1 of adding the condensate (16) back to the solvent distillation step (8) is included in the process to collect further active compounds.

4.1 Skin Treatment

4.1.1 Psoriasis

The ethanol solution (35) extracted above was tested on a psoriasis sufferer without success but when mixed with oil extract (12) from Example 1 it did have a healing effect on psoriasis symptoms. During trials it was found that moisturising oil (not shown) was a requirement to allow the GSL, TCL and ITCL to penetrate through the plaque on the skin. This result suggests to the applicant that while active component is present in this manufacturing process, a carrier base i.e. oil is necessary as well to be effective in treatment of psoriasis.

Extraction Example 5

Figure 4:
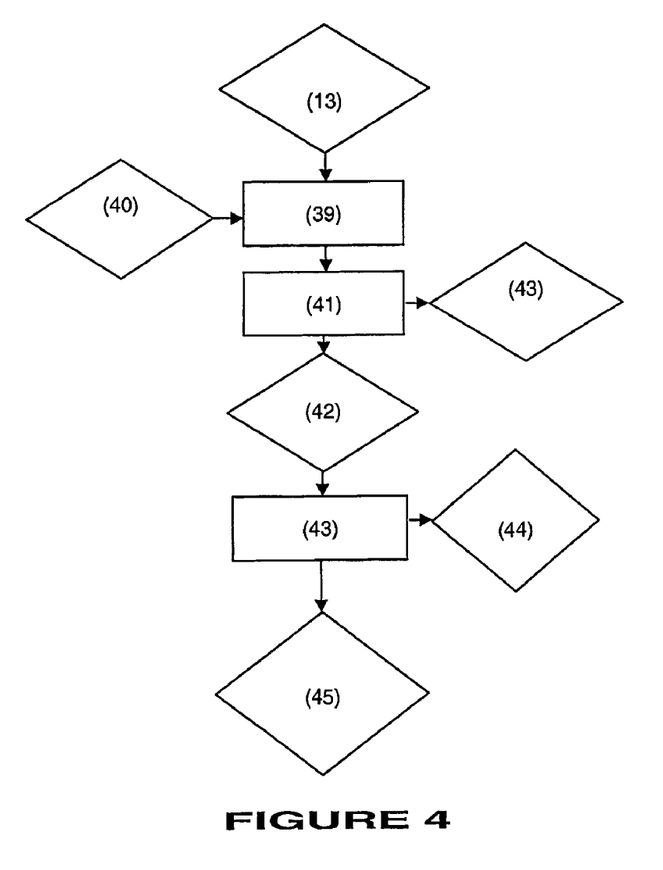
FIG. 4 is a process flow diagram for a further alternative extraction step to produce a light oil fraction rich in GSL, ITCL and TCL compounds.

Referring to FIG. 4, the extracted seed (13) in Example 1 was thoroughly mixed (39) with water (40) and allowed to settle. The resulting water solution (42) was decanted off (41), filtered and dried (43) to give a light oil fraction (45).

Infra-red analysis of the light oil fraction (45) showed benzene ring overtones and sulfoxide absorption at the same peaks to that found in Example 4 above.

Extraction Example 6

Figure 5:
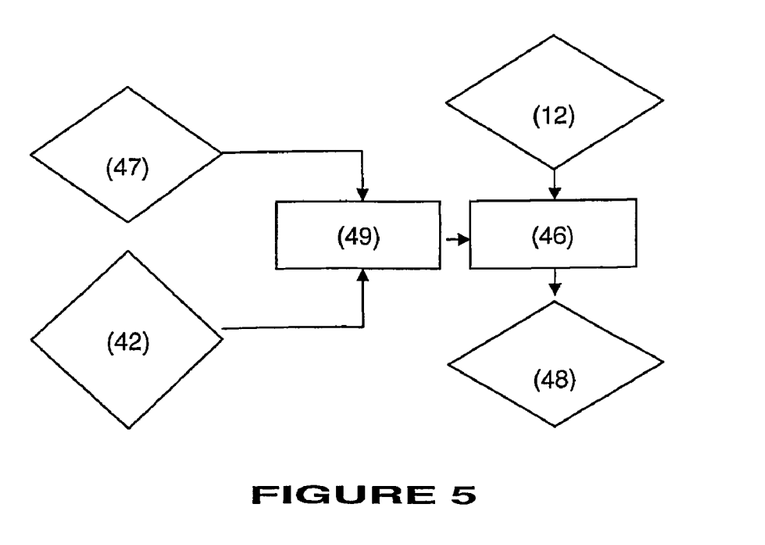
FIG. 5 is a process flow diagram for a further extraction step to form a medicament.

Referring to FIG. 5, a cream/ointment medicament (48) using oil extract (12) from Example 1 is formed by mixing (46) the oil extract (12) and a cream or ointment base (47) together. In the applicant's experience, a solution containing up to 30% wt oil extract (12) is preferable.

Additional active compounds of GSL, ITCL and TCL can be integrated into the mixture by mixing (49) the water solution (42) of Example 5 into the cream or ointment base (47) and then mixing (46) this with the oil extract (12) to form a medicament (48).

6.1 Skin Treatment

6.1.1 Psoriasis

The resulting creams and ointments (48) have been tested on psoriasis symptoms and similar effects to that of the above Examples 1, 2, and 4 have been found in treatment of psoriasis.

Extraction Example 7

Figure 6:
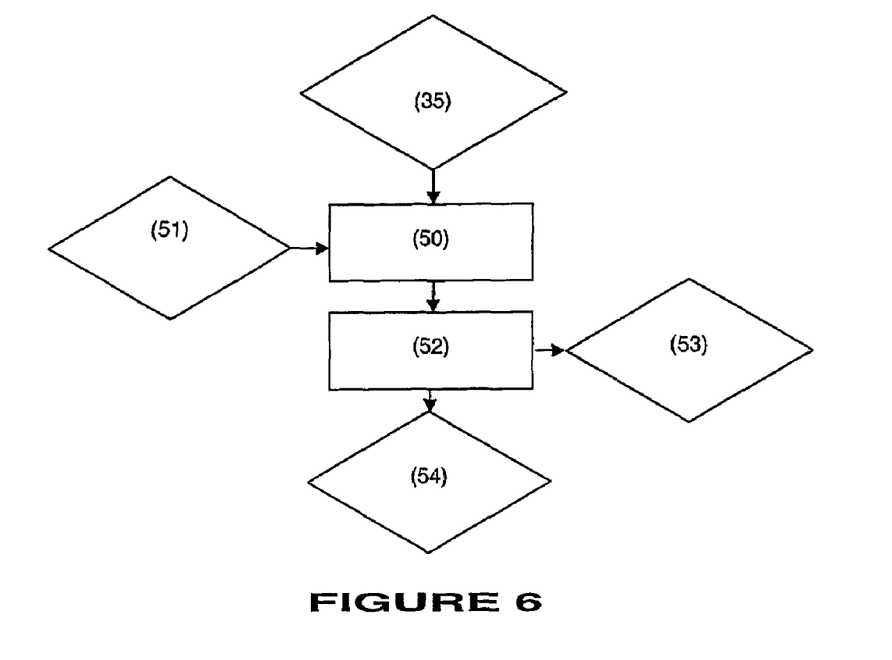
FIG. 6 is a process flow diagram for a further extraction step to form an oil solution after FIG. 3 in a further embodiment of the invention.

Referring to FIG. 6, the ethanol solution (35) of Example 4 was mixed (54) with canola oil (51). The ethanol (53) was evaporated off in an oven set at 55° C. The resulting oil solution (54) was collected.

7.1 Skin Treatment

7.1.1 Psoriasis

The oil solution (54) was applied to the skin of a psoriasis condition in order to ascertain the healing effects of the solution (54). A limited effect was noted in healing the psoriasis however less than that found in the other examples above.

Extraction Example 8

Figure 7:
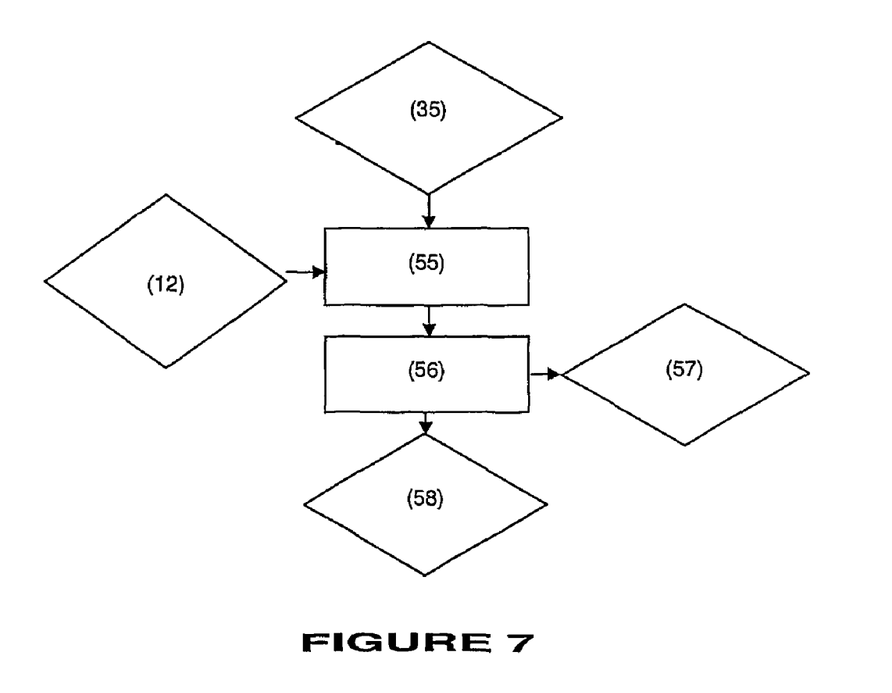
FIG. 7 is a process flow diagram for an alternative further extraction step to form an oil solution after FIG. 3 in a further embodiment of the invention.

Referring to FIG. 7, the ethanol solution (35) of Example 4 was mixed (55) with the oil extract (12) from Example 1. As in Example 7, the ethanol (57) was evaporated (56) off in an oven set at 55° C. The resulting oil solution (58) was collected.

8.1 Skin Treatment
8.1.1 Psoriasis

The oil solution (58) was applied to the skin of a psoriasis condition in order to ascertain the healing effects of the solution. The same healing effect was noted as for examples 1, 2, 4 and 6 above.

Aspects of the present invention have been described by way of example only and it should be appreciated that modifications and additions may be made thereto without departing from the scope thereof as defined in the appended claims.

What we claim is:

1. A method of producing an oil extract from seeds of plants selected from the group including: meadowfoam; brassicas; crambe; said method including the steps of:
   (a) washing the seed with a solvent, whereby oil from the seed is dissolved in the solvent;
   (b) separating a spent seed solvent solution, wherein the spent seed solvent solution is a binary azeotropic mixture of aliphatic solvents and alcohols;
   (c) distilling the spent seed solvent solution at a temperature of equal to or less than 120° C., and a pressure equal to or less than 50 kPa to obtain an oil extract from the spent seed solvent solution; and
   (d) deodorising the oil extract to remove any adverse odours in the oil extract,
   wherein the oil extract produced contains a glucosinolates (GSL).

2. The method as claimed in claim 1, wherein the oil extract also contains isothiocyanate (ITCL) and thiocyanate (TCL).

3. The method as claimed in claim 1, wherein the oil extract also contains nitrile thiones and phenolic compounds.

4. The method as claimed in claim 1 wherein the solvent is a binary azeotropic mixture of hexane and ethanol.

5. The method as claimed in claim 4, wherein the azeotropic mixture is approximately 79% hexane and 21% ethanol.

6. The method as claimed in claim 1, wherein solvent distilled from the oil extract in step (c) is recycled into the washing step (a).

7. The method as claimed in claim 1, wherein the seeds are dressed and dried before step (a).

8. The method as claimed in claim 1, wherein the seeds are crushed before step (a).

9. The method as claimed in claim 1, wherein the seeds are crushed to a flaked condition before step (a).

10. The method as claimed in claim 1, further comprising, after step (b), storing the oil extract and allowing seek husk residue to settle and be filtered from the oil.

11. The method as claimed in claim 1, wherein said deodorising comprises adding water to the oil extract and subsequently boiling off the water and residual solvent, leaving a deodorised oil extract.

12. The method as claimed in claim 11, wherein the boiling occurs in an oven heated to a temperature less than 120° C.

13. The method as claimed in claim 11, wherein the boiling occurs in an oven heated to a temperature less than 80° C.

14. The method as claimed in claim 1, wherein said deodorising comprises adding a masking substance to the oil extract.

15. The method as claimed in claim 1, further comprising, after step (b), drying the spent seeds to separate remaining solvent as a condensate.

16. The method as claimed in claim 15, wherein the drying is by a combination of steam treatment, under a vacuum, and the application of heat.

17. The method as claimed in claim 15, wherein said condensate is added to the solvent solution during step (b).

18. A method of producing a light oil fraction from seeds of plants selected from the group consisting of: meadowfoam, brassicas, and crambe; the method comprising the steps of:
   (i) forming a mixture from the oil extract, said oil extract comprising glucosinolates (GSL), isothiocyanate (ITCL) and thiocyanate (TCL) wherein the extract is derived from meadowfoam, with a solvent selected from the group consisting of:
   alcohol; water; and a combination thereof; and
   (ii) separating the mixture of step (i) into a solvent solution and oil;
   (iii) drying the solvent solution from step (ii) to remove solvent; and
   (iv) collecting the light oil fraction.

19. The method as claimed in claim 18, wherein approximately equal volumes of the solvent and the oil extract are mixed.

20. The method as claimed in claim 18, wherein the alcohol is selected from the group consisting of: methanol; ethanol; other lower alcohols; and any combination thereof.

21. A method as claimed in claim 18, wherein steps (i) to (iv) are repeated one or more times.

22. A method of producing a light oil fraction from seeds of plants selected from the group consisting of: meadowfoam, brassicas, and crambe, the method comprising the steps of:
   (i) mixing the oil extract, said oil extract comprising glucosinolates (GSL), isothiocyanate (ITCL) and thiocyanate (TCL) wherein the extract is derived from meadowfoam, with at least one alcohol to make a first alcohol solution;
   (ii) separating the first alcohol solution from the oil;
   (iii) mixing the oil from step (ii) with at least one other alcohol to that used in step (i) to make a second alcohol solution;
   (iv) separating the alcohol solution from the oil; and
   (v) drying the alcohol solution and the second alcohol solution either separately or together to remove alcohol solvent and collecting a light oil fraction.

23. The method as claimed in claim 22, wherein approximately equal volumes of alcohol and oil extract are mixed in steps (i) and (iii).

24. The method as claimed in claim 22, wherein the alcohol in step (i) is methanol and the alcohol in step (iii) is ethanol.

25. The method as claimed in claim 18, wherein the light oil fraction contains glucosinolates (GSL).

26. The method as claimed in claim 25, wherein the light oil fraction also contains isothiocyanate (ITCL) and thiocyanate (TCL).

27. The method as claimed in claim 25, wherein the light oil fraction contains nitrile thiones and phenolic compounds.

28. A method of producing an aqueous solution from the seeds of plants selected from the group consisting of: meadowfoam, brassicas, and crambe; the method comprising the step of: mixing the oil extract, said oil extract comprising glucosinolates (GSL), isothiocyanate (ITCL) and thiocyanate (TCL) wherein the extract is derived from meadowfoam, with a base aqueous solution.

29. The method as claimed in claim 28, wherein a light oil fraction is further mixed into the base aqueous solution, the light oil fraction being produced from seeds of plants selected from the group consisting of: meadowfoam, brassicas, and crambe; and said light oil fraction being produced by a method comprising the steps of:
- (a) washing the seeds with a solvent, whereby oil from the seeds is dissolved in the solvent;
- (b) separating spent seed and solvent solution;
- (c) distilling the solvent solution at a temperature of equal to or less than 120° C., and a pressure equal to or less than 50 kPa to obtain an oil extract from the solvent solution, wherein the oil extract produced contains glucosinolates (GSL);
- (d) forming a mixture from the oil extract with a solvent selected from the group consisting of: alcohol, water, and combinations thereof;
- (e) separating the mixture of step (d) into a solvent solution and oil; and
- (f) drying the solvent solution of step (e) to remove solvent and collecting the light oil fraction.

30. The method as claimed in claim 28, wherein the oil extract, and light oil fraction, forms 1 to 50% wt of the combined mixture.

31. The method as claimed in claim 28, wherein the base aqueous solution has a water component.

32. The method as claimed in claim 28, wherein the base aqueous solution is a cream or ointment.

33. The method as claimed in claim 22, wherein the light oil fraction contains glucosinolates (GSL).

34. A filtered oil extract comprising an extract of meadowfoam, said filtered oil extract containing glucosinolates (GSL), isothiocyanate (ITCL) and thiocyanate (TCL) compounds in therapeutically effective amounts.

* * * * *